(12) United States Patent
Bornhoft

(10) Patent No.: US 9,272,088 B2
(45) Date of Patent: Mar. 1, 2016

(54) INTRAVENOUS CATHETER INSERTER

(75) Inventor: Stephen Bornhoft, Midvale, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 631 days.

(21) Appl. No.: 13/615,012

(22) Filed: Sep. 13, 2012

(65) Prior Publication Data

US 2014/0074032 A1    Mar. 13, 2014

(51) Int. Cl.
*A61M 25/00* (2006.01)
*A61M 5/158* (2006.01)
*A61M 25/06* (2006.01)
A61M 39/06 (2006.01)
A61M 39/10 (2006.01)

(52) U.S. Cl.
CPC ........... *A61M 5/158* (2013.01); *A61M 25/0606* (2013.01); *A61M 25/0625* (2013.01); *A61M 25/0631* (2013.01); *A61M 39/0693* (2013.01); *A61M 2005/1585* (2013.01); *A61M 2039/062* (2013.01); *A61M 2039/1072* (2013.01); *Y10T 29/4984* (2015.01)

(58) Field of Classification Search
CPC ...... A61M 25/0606; A61M 25/0612–25/0631; A61M 2025/0253–2025/0266; A61M 2039/0633; A61M 2039/0686; A61M 39/0693
USPC ............. 604/164.01, 164.04, 164.06–164.08, 604/167.01, 167.02, 174, 180
See application file for complete search history.

(56) References Cited

U.S. PATENT DOCUMENTS

| | | | |
|---|---|---|---|
| 4,488,545 A | 12/1984 | Shen | |
| 5,251,873 A | 10/1993 | Atkinson et al. | |
| 5,531,720 A * | 7/1996 | Atkins | 604/537 |
| 5,632,729 A | 5/1997 | Cai et al. | |
| 5,833,213 A | 11/1998 | Ryan | |
| 7,455,663 B2 | 11/2008 | Bikovsky | |
| 7,666,166 B1 * | 2/2010 | Emmert et al. | 604/167.02 |
| 2002/0161332 A1 | 10/2002 | Ramey | |
| 2003/0229308 A1 | 12/2003 | Tsals et al. | |
| 2007/0185441 A1 | 8/2007 | Fangrow, Jr. | |
| 2008/0154205 A1* | 6/2008 | Wojcik | 604/164.01 |
| 2010/0204675 A1* | 8/2010 | Woehr et al. | 604/500 |
| 2011/0160662 A1 | 6/2011 | Stout et al. | |
| 2012/0197204 A1 | 8/2012 | Helm, Jr. | |
| 2012/0226239 A1 | 9/2012 | Green | |

FOREIGN PATENT DOCUMENTS

| | | | |
|---|---|---|---|
| EP | 1 776 980 A1 | 4/2007 |
| EP | 2 364 738 A2 | 9/2011 |

(Continued)

*Primary Examiner* — Nicholas Lucchesi
*Assistant Examiner* — Anh Bui
(74) *Attorney, Agent, or Firm* — Jeanne Lukasavage; Craig Metcalf; Kirton McConkie

(57) ABSTRACT

An intravenous catheter inserter device comprising a catheter threader body on which is slidably attached a septum activator, a catheter threader, and a needle hub. Some embodiments further include a safety bar that is configured to assist in coordinating the movement of the various components of the device during a catheterization procedure. In general, the septum activator provides a pathway through a septum of a Luer adapter. The Luer adapter comprises a wedge seal that is configured to receive a base portion of a catheter that is inserted into the Luer adapter by the catheter threader. Accordingly, the device of the present invention simultaneously accesses the vasculature of a patient while assembling the catheter into the Luer adapter. The final configuration provides an integrated unit that is attached to the patient and in fluid communication with patient's vascular system.

20 Claims, 13 Drawing Sheets

(56) References Cited

FOREIGN PATENT DOCUMENTS

| | | |
|---|---|---|
| EP | 2 399 624 A1 | 12/2011 |
| EP | 2 433 663 A1 | 3/2012 |
| WO | 2006/062636 A1 | 6/2006 |
| WO | 2008/133702 A1 | 11/2008 |
| WO | 2011/089193 A2 | 7/2011 |
| WO | 2011/121023 A1 | 10/2011 |

* cited by examiner

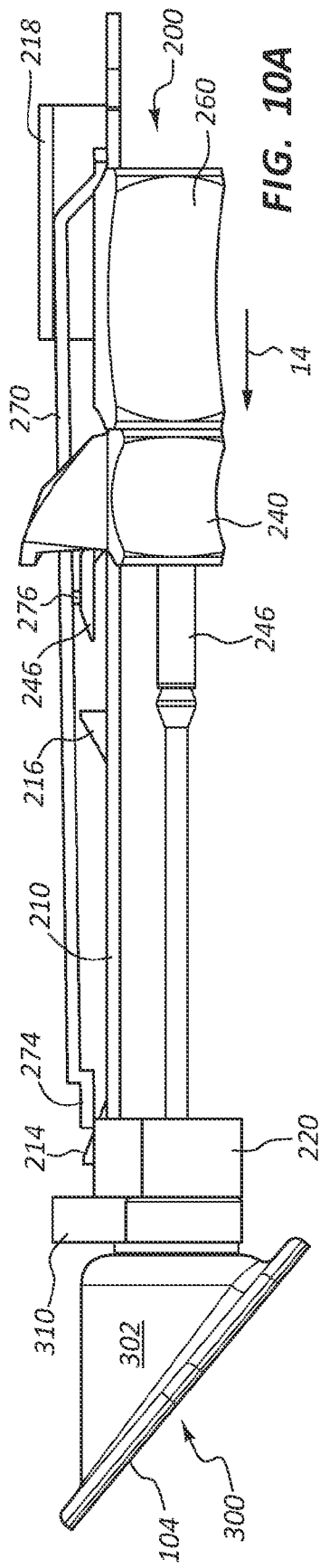
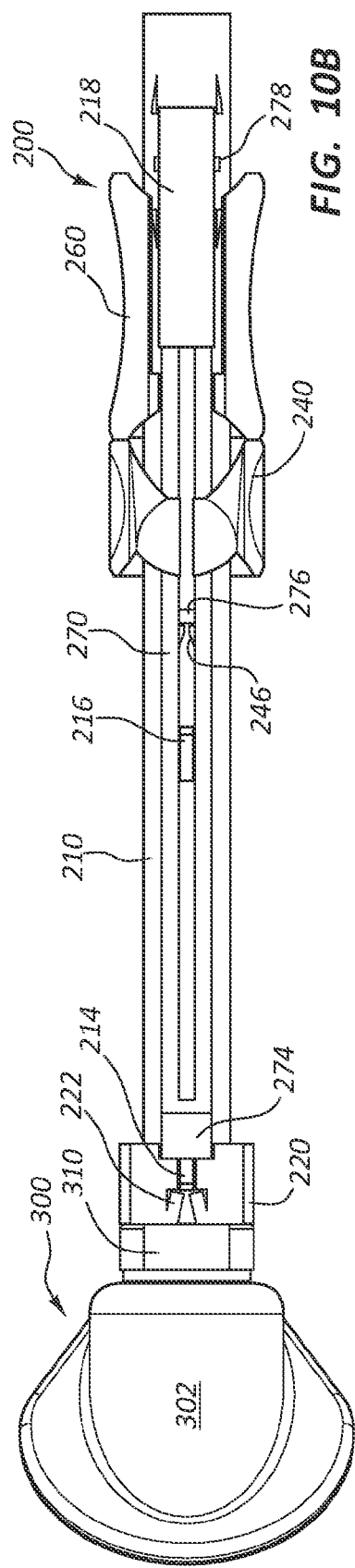
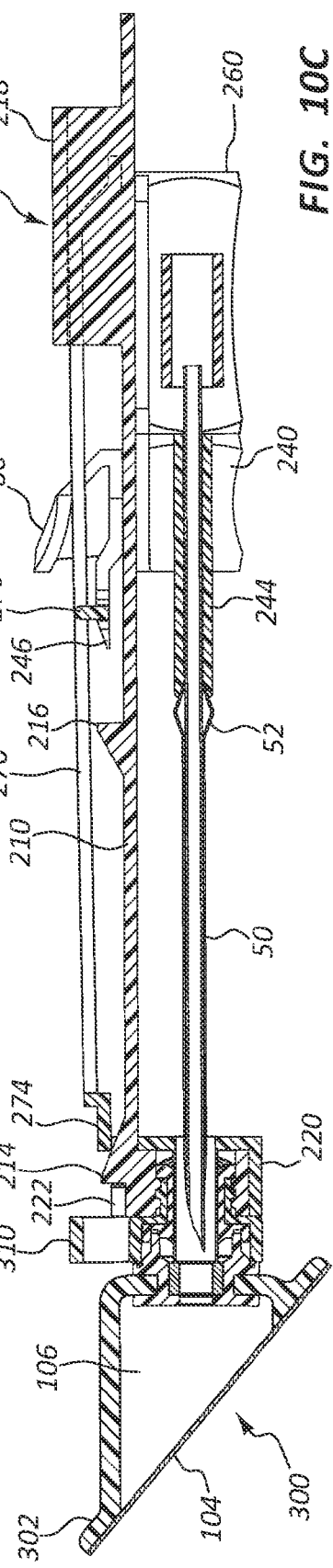

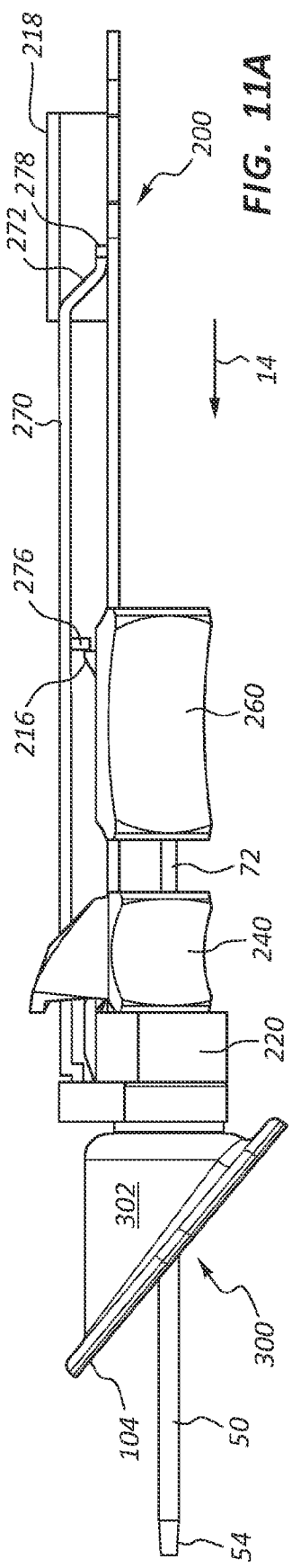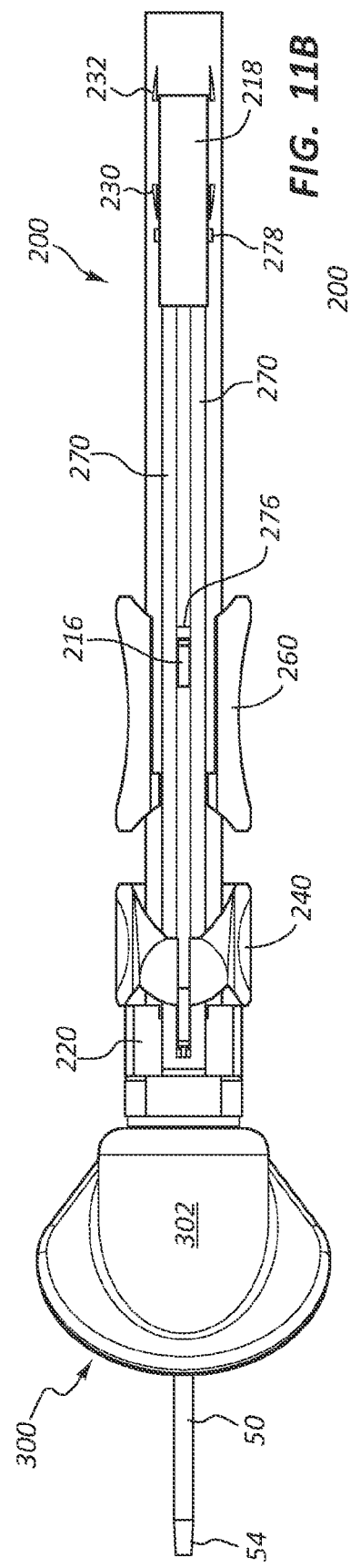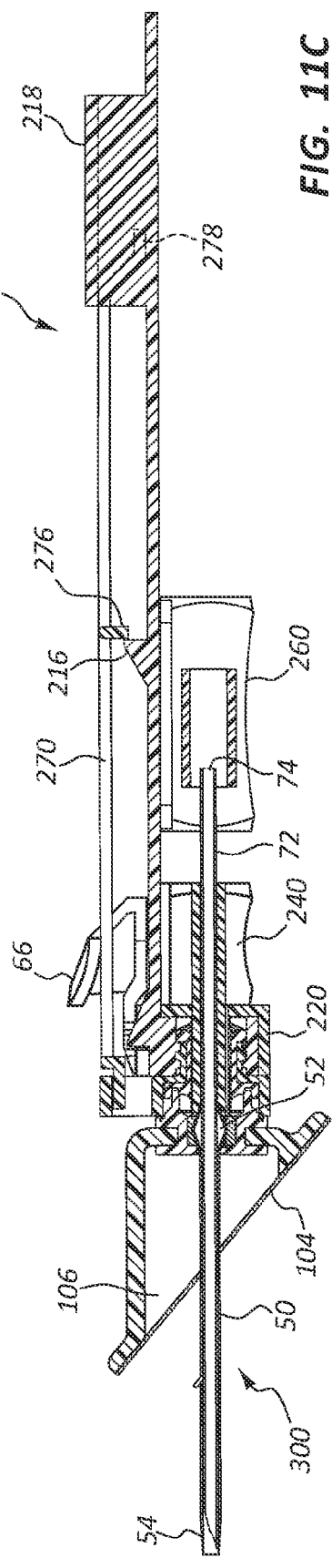

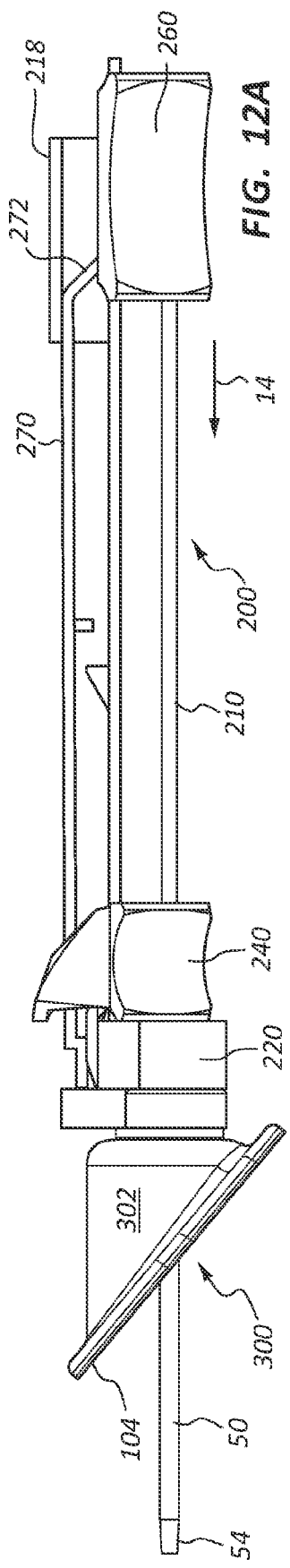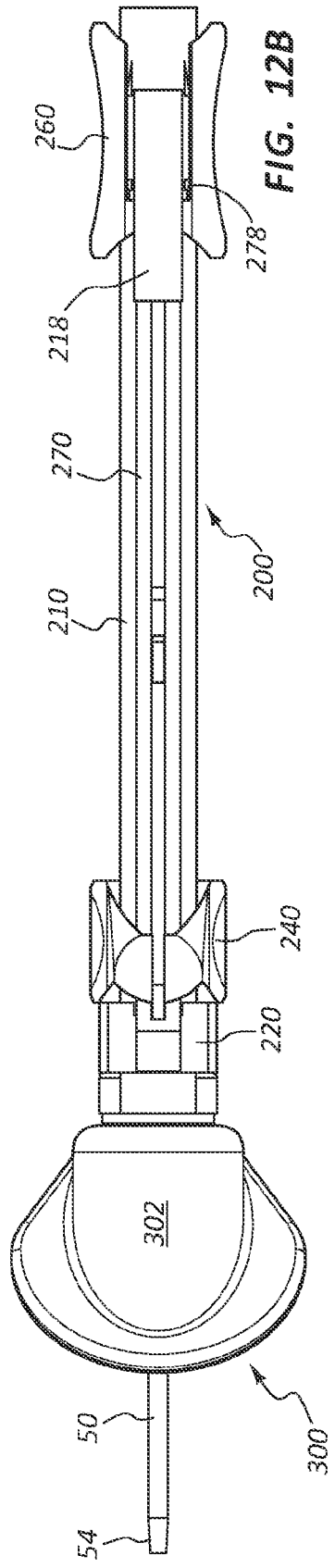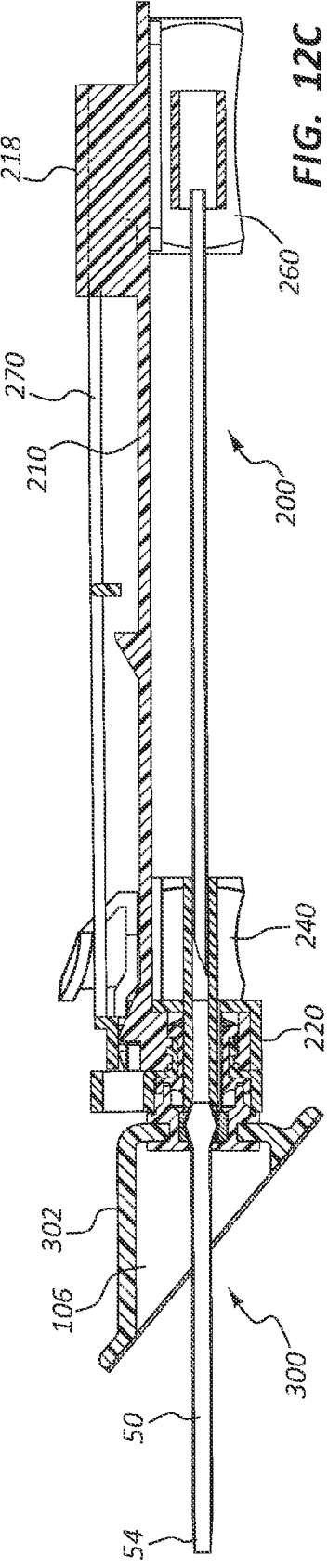

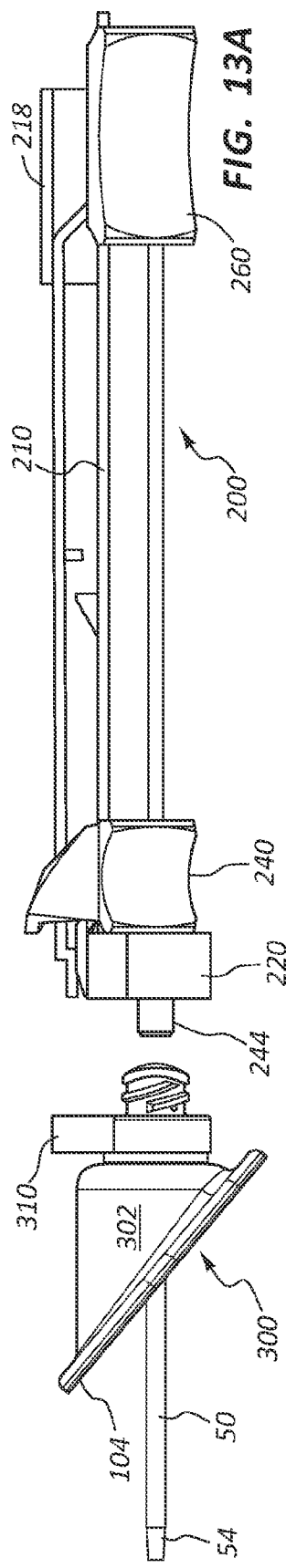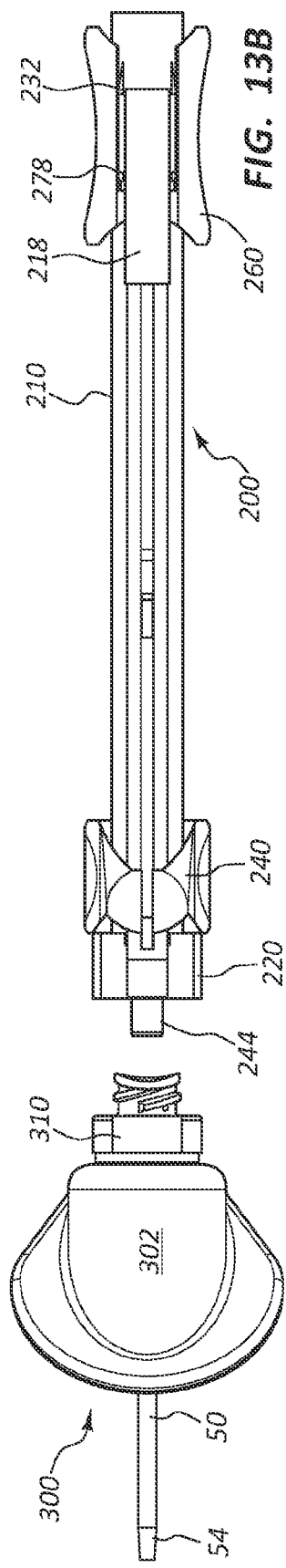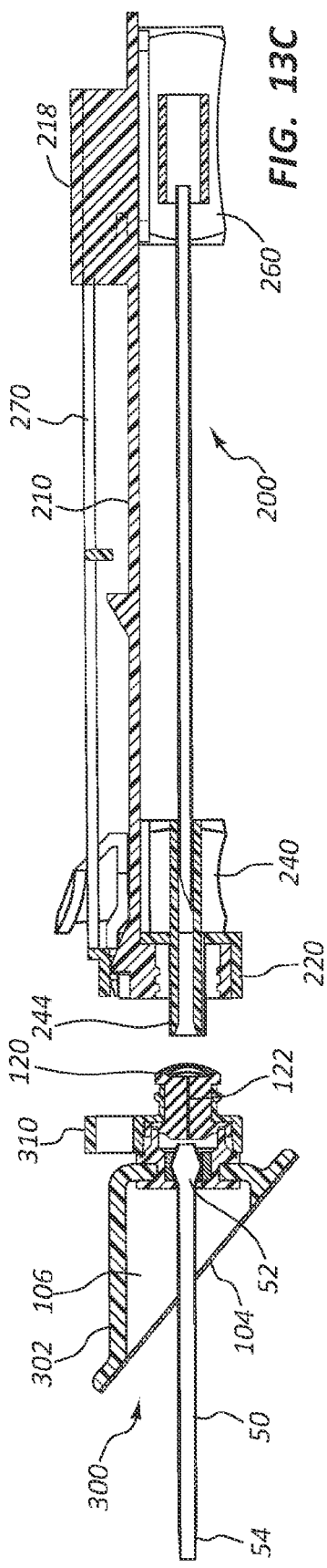

INTRAVENOUS CATHETER INSERTER

BACKGROUND OF THE INVENTION

This disclosure relates generally to intravenous catheters and Luer devices. More specifically, this disclosure discusses an intravenous catheter inserter that comprises a Luer adapter having a wedge seal disposed therein that is configured to receive a base portion of catheter during a catheterization procedure. The intravenous catheter inserter device includes a catheter inserter body that is coupled to the Luer adapter, wherein the catheter inserter body comprises various components to facilitate simultaneous catheterization of a patient while advancing and securing a base portion of the catheter into the wedge seal of the Luer adapter.

As used herein, the term "Luer" is understood to describe and include any Luer taper or other system of small-scale fluid fittings used for making leak-free connections between a male-taper fitting and its mating female part on medical devices and/or equipment. A Luer device or adapter in accordance with the present invention may further include an integrated septum, whereby to provide selective access between two devices interconnected via a Luer fitting connection. Non-limiting examples of Luer fittings include "Luer-Lok," "Luer-Slip," and "Nexiva Closed IV Catheter" systems produced by Becton Dickenson, Inc.

Infusion therapy involves the administration of a fluid to a patient through a needle or catheter. It is generally prescribed when a patient's treatment cannot be treated effectively by oral medication. Typically, "infusion therapy" refers to procedures where a drug or other fluid is administered intravenously. However, the term also refers to situations where fluids are provided through other non-oral routes, such as intramuscular injections, subcutaneous injections, and epidural routes.

Intravenous infusion therapies are generally used to introduce to or remove fluid from a patient. The infusion process generally requires steady control of the catheter and needle to ensure proper vascular access while avoiding or minimizing injury to the patient. In emergency situations, such as in the back of a moving ambulance, a physician or other caregiver may be incapable of inserting a catheter into a patient due to excessive movement of the patient's surrounding. As such, the ambulance is required to stop to allow the caregiver a steady environment in which to insert the catheter. This creates an inconvenience to the caregiver and wastes valuable time that may be needed to save the life of the patient. Accordingly, there is a need in the art for a device which overcomes the difficulties and shortcomings associated with currently available technologies. The present disclosure discusses such a device.

BRIEF SUMMARY OF THE INVENTION

The present invention provides an intravenous catheter inserter that includes a Luer adapter removably coupled to a catheter inserter body. The Luer adapter includes a flexible hood having a base configured to attach to a surface of a patient, thereby forming a secure interface with the patient. The Luer adapter further includes a wedge seal configured to receive a base portion of a catheter that is inserted into the Luer adapter via the catheter inserter body. The Luer adapter further includes a septum. Some embodiments further include a rotational block that is configured to prevent premature separation of the Luer adapter from a catheter inserter The catheter inserter body includes various components to enable simultaneous catheterization of a patient while fully seating the catheter into the wedge seal of the Luer adapter. In some instances the catheter inserter body comprises a septum activator having a distal end that is inserted through the septum to provide a pathway there through. The catheter inserter body further includes a catheter threader that advances a catheter through the septum (via the septum activator) and into the patient at a maximum depth which results in the base portion of the catheter being fully seated into the wedge seal.

A needle is also provided and coupled to a needle hub that is slidably coupled to the catheter inserter body. The needle comprises a sharpened tip that is exposed distally past a tip of the catheter. The sharpened tip of the needle provides an opening into the vasculature of the patient through which the catheter is inserted. In some implementations, the needle hub and the catheter threader are advanced together to achieve catheterization. Following catheterization, the needle and catheter threader are withdrawn from the Luer adapter. The catheter inserter body is then removed from the Luer adapter and discarded.

The present invention further includes one or more methods for manufacturing an intravenous catheter inserter. In some implementations, a method for manufacturing an intravenous catheter inserter includes steps for 1) providing a Luer adapter having a first end comprising a septum and a second end comprising a catheter hood having a base; 2) positioning a wedge seal within the Luer adapter at a position between the first and second ends; 3) providing an inserter body having a distal end for receiving the first end of the Luer adapter; 4) slidably coupling a septum activator to the inserter body, a distal portion of the septum activator being configured to provide a pathway through the septum, the septum activator further having an opening; 5) slidably coupling a catheter threader to the inserter body, the catheter threader having a probe for contacting a base portion of a catheter, the probe being configured to advance the base portion of the catheter through the opening of the septum activator and the pathway through the septum and into the wedge seal, the wedge seal being configured to retain the catheter and form a fluid-tight seal between the base portion and the wedge seal, the probe further having an opening for providing a pathway through the probe; and 6) slidably coupling a needle hub to the inserter body, the needle hub having a needle which extends through the opening of the probe, the opening of the septum activator, and the catheter, wherein the needle assists in inserting the catheter into a patient. The method may further include a step for providing a window in the inserter body to provide access to the septum activator, the catheter threader, and the needle hub. Some methods may further include a step for providing a safety bar having a first end and a second end, the first end being slidably coupled to the needle hub, the second end extending distally from the needle hub and being positioned adjacent to a distal end of the catheter inserter body.

Some methods of the present invention further include a step for providing a clip on the catheter threader, the clip being configured to retain a tab of the safety bar. Other methods may include a step for providing a splitter on the catheter inserter body which is configured to contact the clip of the catheter threader and release the tab of the safety bar as the catheter threader and the safety bar are moved in a distal direction, and wherein contact between the splitter and the tab of the safety bar limits movement of the safety bar in the distal direction. Further, some methods include steps for 1) providing a ramp on the distal end of the catheter inserter body; 2) providing a rotational block on the Luer adapter; and 3) providing a clip on the septum activator, the clip being configured to receive the ramp and lock the septum activator to the ramp in a locked position, the locked position resulting in the distal portion of the septum activator being inserted through the septum to provide the pathway through the septum, the ramp further comprising an inclined surface which is contacted by the second end of the safety bar as the needle hub and the safety bar are moved in a distal direction, wherein contact between the inclined surface and the safety bar lifts the second end of the safety bar over the septum activator to insert the second end of the safety bar into the rotational block.

BRIEF DESCRIPTION OF THE SEVERAL VIEWS OF THE DRAWINGS

In order that the manner in which the above-recited and other features and advantages of the invention are obtained and will be readily understood, a more particular description of the invention briefly described above will be rendered by reference to specific embodiments thereof, which are illustrated in the appended drawings. Understanding that these drawings depict only typical embodiments of the invention and are not, therefore, to be considered to be limiting of its scope, the invention will be described and explained with additional specificity and detail through the use of the accompanying drawings in which:

FIG. 10, shown in parts A, B, and C, illustrates a perspective side, a perspective top, and a cross-section side view of an intravenous catheter inserter following actuation of the septum of the Luer adapter via the septum actuator in accordance with a representative embodiment of the present invention.

FIG. 11, shown in parts A, B, and C, illustrates a perspective side, a perspective top, and a cross-section side view of an intravenous catheter inserter having the needle and catheter fully extended such that a base portion of the catheter is fully seated into a wedge seal of the Luer adapter in accordance with a representative embodiment of the present invention.

FIG. 12, shown in parts A, B, and C, illustrates a perspective side, a perspective top, and a cross-section side view of an intravenous catheter inserter following the withdrawal of the needle from the fully seated catheter in accordance with a representative embodiment of the present invention.

FIG. 13, shown in parts A, B, and C, illustrates a perspective side, a perspective top, and a cross-section side view of an intravenous catheter inserter following the withdrawal of the probe portion of the catheter threader from the septum actuator and further following the detachment of the Luer adapter from the intravenous catheter inserter in accordance with a representative embodiment of the present invention.

DETAILED DESCRIPTION OF THE INVENTION

Figure 1:
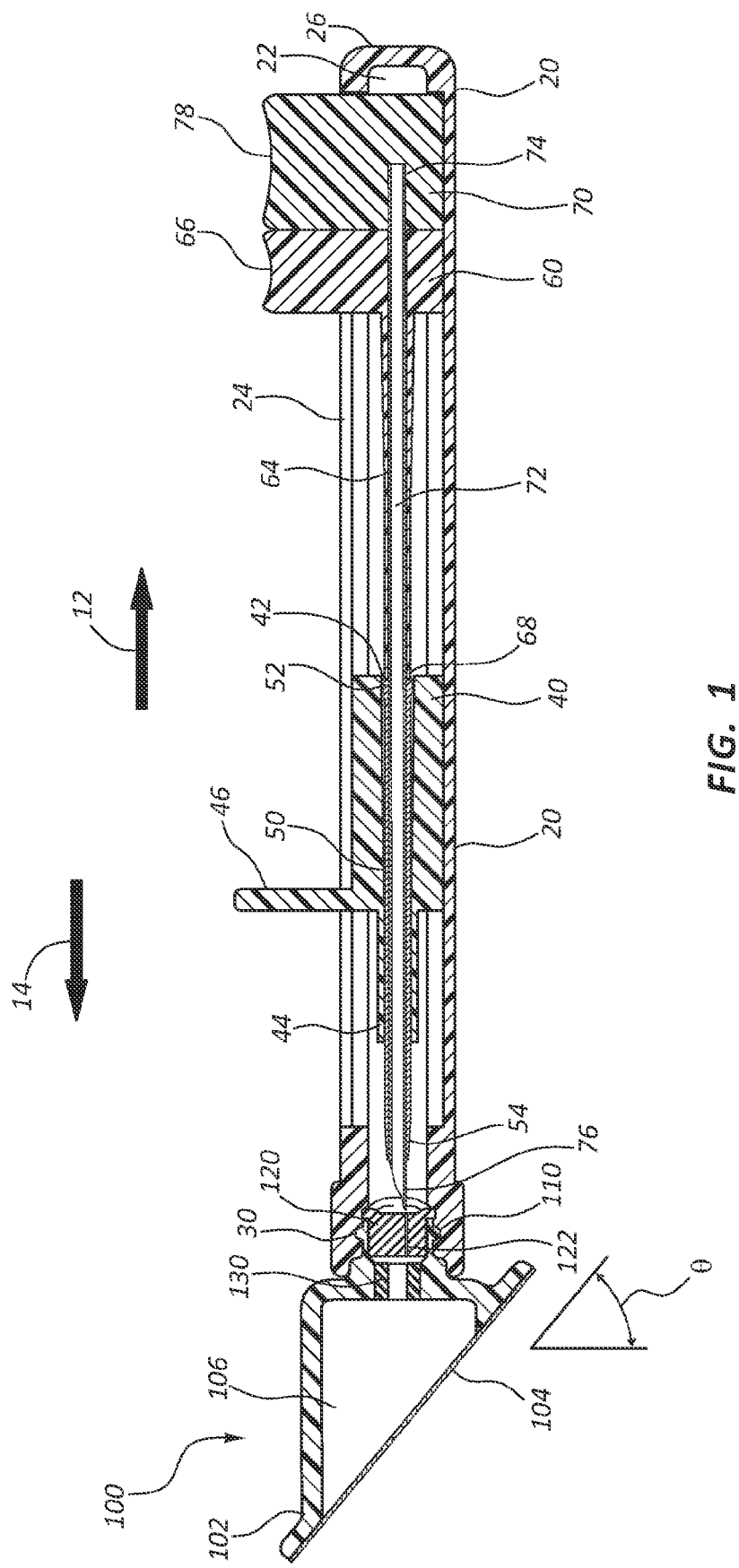
FIG. 1 illustrates a cross-section side view of an intravenous catheter inserter prior to being inserted into a patient in accordance with a representative embodiment of the present invention.

The presently preferred embodiments of the described invention will be best understood by reference to the Figures, wherein like parts are designated by like numerals throughout. It will be readily understood that the components of the present invention, as generally described and illustrated in the accompanying Figures, could be arranged and designed in a wide variety of different configurations. Thus, the following more detailed description of some embodiments of the invention, as represented in the Figures, is not intended to limit the scope of the invention, as claimed, but is merely representative of some presently preferred embodiments of the invention.

Generally, the present invention relates to an integrated unit for securing a catheter and a Luer access device to a patient. In particular, some embodiments of the present invention provide a handheld device which includes a catheter inserter body which is selectively coupled to a Luer adapter. In some instances, the Luer adapter comprises a hood made of a flexible polymer material which comprises a base configured to form an interface with a body surface of a patient. In some embodiments, the base of the Luer adapter further comprises an adhesive to secure and fix the location of the Luer adapter on the patient. Non-limiting examples of a compatible Luer adapter is provided in U.S. patent application Ser. No. 13/614,481, titled LUER SECUREMENT DEVICE, filed Sep. 13, 2012 by Stephen Bornhoft, which is incorporated herein by reference in its entirety.

The catheter inserter body is selectively coupled to the Luer adapter in a removable manner. The Luer adapter is secured to the patient via an adhesive. The interconnected Luer adapter and catheter inserter body provides a bridged connected between the patient and the user. As such, the user is not affected by external movements that may otherwise disturb a catheterization procedure. The flexible nature of the hood of the Luer adapter further permits the user to make small adjustments during the catheterization procedure to ensure proper insertion. Following insertion of the catheter into the vasculature of the patient, the catheter inserter body is removed from the Luer adapter and discarded. The Luer adapter remains in place thereby securing the inserted position of the catheter and allowing fluid access to the patient.

The embodiments of the present invention further include a catheter. The catheter of the present invention may include any type or style of catheter compatible with in vitro use. For example, in some instances the present invention includes an intravenous catheter. Accordingly, catheters compatible with the present invention may include flexible, polymer catheters and/or rigid polymer or metallic catheters, as may be desired.

The catheter inserter comprises various components to facilitate the catheterization of the patient. In particular, the catheter inserter comprises a septum activator which is slidably coupled to the body of the catheter inserter. The septum activator is configured to be slid in a distal direction whereupon a distal portion of the septum activator is advanced through a septum of the Luer adapter to provide a pathway there through. This pathway permits insertion of the catheter and needle of the catheter inserter without damaging the septum. Further, this pathway prevents contact between the catheter and the septum during catheterization thereby eliminating frictional resistance and enabling a resistance free insertion of the needle and catheter.

In some embodiments, the catheter inserter further comprises a catheter threader having a probe that advances the catheter through the septum during the catheterization process. This is accomplished as the catheter threader is slid or advanced in a distal direction. In some instances, the catheter threader is slidably coupled to the body of the catheter inserter. The catheter inserter further comprises a needle hub that is similarly coupled to the body of the catheter inserter. The needle hub comprises a needle having a first end that is fixedly coupled to the needle hub, and further includes a second end comprising a sharpened tip that is configured to puncture the skin and vein of the patient to provide an opening through which the catheter may be inserted and advanced. A body of the needle is threaded through the catheter threader and the catheter such that the sharpened tip of the needle is exposed beyond a tip of the catheter. This type of intravenous catheter is commonly known in the art as an "over-the-needle catheter."

The Luer adapter of the present invention further comprises a wedge seal having an annular shape configured to receive a base portion of the catheter in a fluid-tight manner. The process of catheterization simultaneously inserts the tip portion of the catheter into the patient as the base portion of the catheter is seated into the wedge seal. When the base portion of the catheter is fully seated into the wedge seal, the maximum depth of insertion of the catheter tip is achieved. The catheterization process is completed as the needle is withdrawn from the catheter, the catheter threader is retracted in a proximal direction, the septum activator is withdrawn from the septum, and the catheter inserter is removed from the Luer adapter. In some embodiments, the septum of the Luer adapter comprises a self-sealing slit, such that upon withdrawing the septum activator, the septum is sealed thereby containing blood from the catheter within the Luer adapter.

One having skill in the art will appreciate that the above-mentioned features and principles of the present invention may be accomplished by various designs and approaches. Accordingly, the present invention is not limited to any specific design or mechanical construction. However, in an effort to enable one of ordinary skill in the art to practice the present invention, the following non-limiting embodiments are provided with explanation.

Referring now to FIG. 1, an intravenous catheter inserter device 10 is shown. Device 10 generally comprises a catheter inserter body 20 that is selectively coupled to a Luer adapter 100. For example, in some embodiments a distal end of catheter inserter body 20 comprises a set of threads 30 that is configured to compatibly receive a set of threads 110 of a first end of Luer adapter 100. Luer adapter 100 further includes a hood 102 that comprises a flexible polymer material. A second end of Luer adapter 100 and hood 102 comprises a base surface 104 that is configured to attach directly to the surface of a patient prior to catheterization. Generally, base surface 104 comprises an adhesive that secured hood 102 to the patient. The flexible nature of hood 102 permits movement of catheter inserter body 20 without detaching hood 102 from the patient. For example, a user may adjust the position of catheter inserter body 20 during catheterization to ensure proper insertion of the catheter and needle into the vasculature of the patient. In some embodiments, base 104 further comprises a base angle θ that is selected based open a desired angle of insertion for the needle and catheter of device 10.

Luer adapter 100 further comprises a septum 120 having a self-sealing slit 122. Septum 120 provides a physical barrier between the internal space 106 of hood 102 and an external environment. Accordingly, following catheterization, septum 120 contains the patient's blood within Luer adapter 100 thereby preventing exposure to the user.

Luer adapter 100 further comprises a wedge seal 130 that is positioned in hood 102 at a position between septum 120 and interior space 106. Wedge seal 130 is annular shaped and comprises an opening having a width configured to receive a base portion of the catheter of device 10 in a fluid-tight manner.

Catheter inserter body 20 may include an internal lumen 22 in which is slidably housed various components to assist in the catheterization process. For example, in some embodiments lumen 22 comprises a septum activator 40 that is positioned adjacent septum 120. In some embodiments, septum activator 40 comprises an opening 42 that forms a pathway through septum activator 40. Opening 42 is sized to slidably accommodate and permit passage of catheter 50 and probe portion 62 of catheter threader 60. A distal end 44 of septum activator 40 is configured to be advanced through slit 122 of septum 120 to provide a pathway there through. In some embodiments, distal end 44 comprises a chamfered leading edge to facilitate easy insertion of distal end 44 into and through slit 122.

In some embodiments, catheter inserter body 20 comprises a window 24 through which a handle portion 46 of septum activator is extended. Window 24 generally comprises a length that permits movement of septum activator 40 and other components in proximal and distal directions 12 and 14, respectively.

With continued reference to FIG. 1, catheter inserter body 20 further comprises a catheter threader 60 which is slidably housed in internal lumen 22 at a position between septum activator 40 and a proximal end 26 of inserter body 20. Catheter threader comprises an opening 64 having a width sized and configured to slidably accommodate and permit passage of needle 72 of needle hub 70. Catheter inserter 60 further comprises a probe 62 that extends distally from catheter inserter 60. Probe 62 comprises an outer diameter that is sized and configured to slidably insert and pass through opening 42 of septum activator 40. A distal end 68 of probe 62 is further sized and configured to contact and/or receive a base portion 52 of catheter 50. As catheter threader 60 is advanced in distal direction 14, distal end 68 pushes or advances catheter 50 through opening 42 of septum activator and through septum 120 until base portion 52 is seated into wedge seal 130. In some embodiments, catheter threader 60 further comprises a handle 66 that extends through window 24 of catheter inserter body 20 so as to be accessible to a user.

Catheter inserter body 20 further comprises a needle hub 70 which is slidably housed in internal lumen 22 at a position between catheter threader 60 and proximal end 26 of inserter body 20. Needle hub 70 comprises a needle 72 having a first end 74 that is fixedly coupled to needle hub 70, and further having a second end comprising a sharpened tip 76 that is threaded through opening 64 and catheter 50, such that sharpened tip 76 extends distally beyond a tip 54 of catheter 50.

Needle hub 70 further comprises a handle 78 that extends through window 24 of catheter inserter body 20 so as to be accessible to a user.

Figure 2:
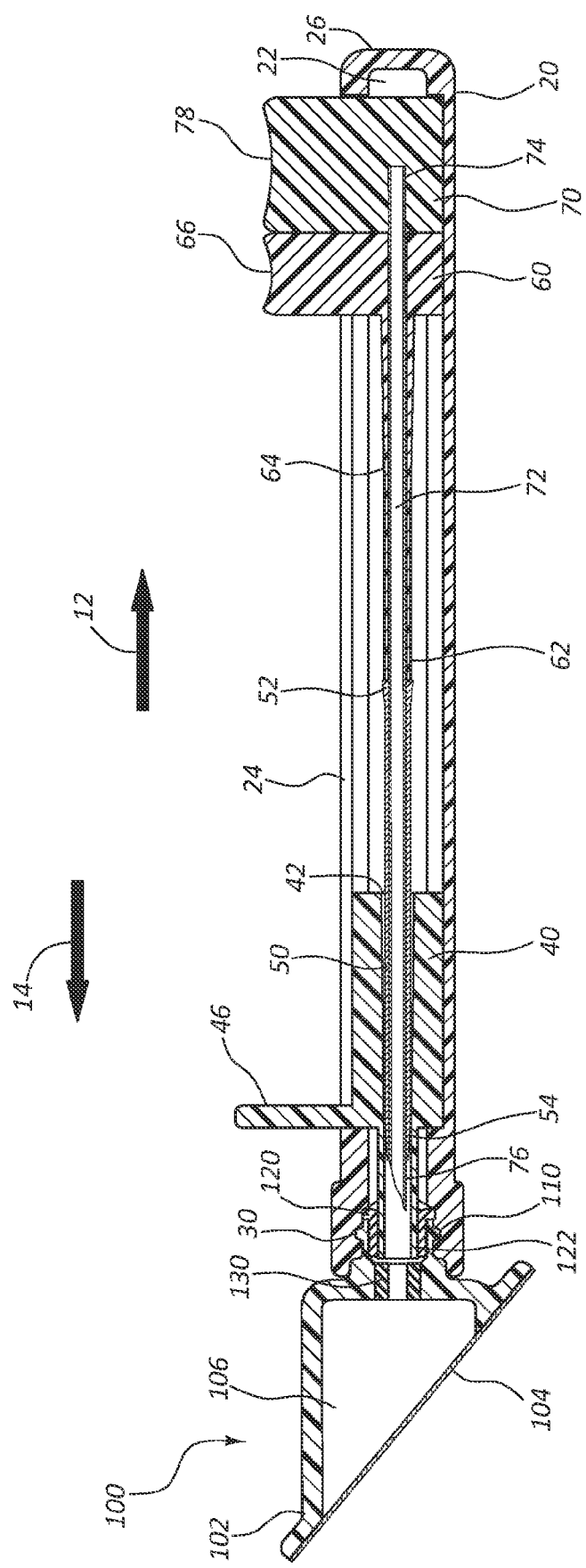
FIG. 2 illustrates a cross-section side view of an intravenous catheter inserter following actuation of the septum of the Luer adapter via the septum actuator in accordance with a representative embodiment of the present invention.
Figure 3:
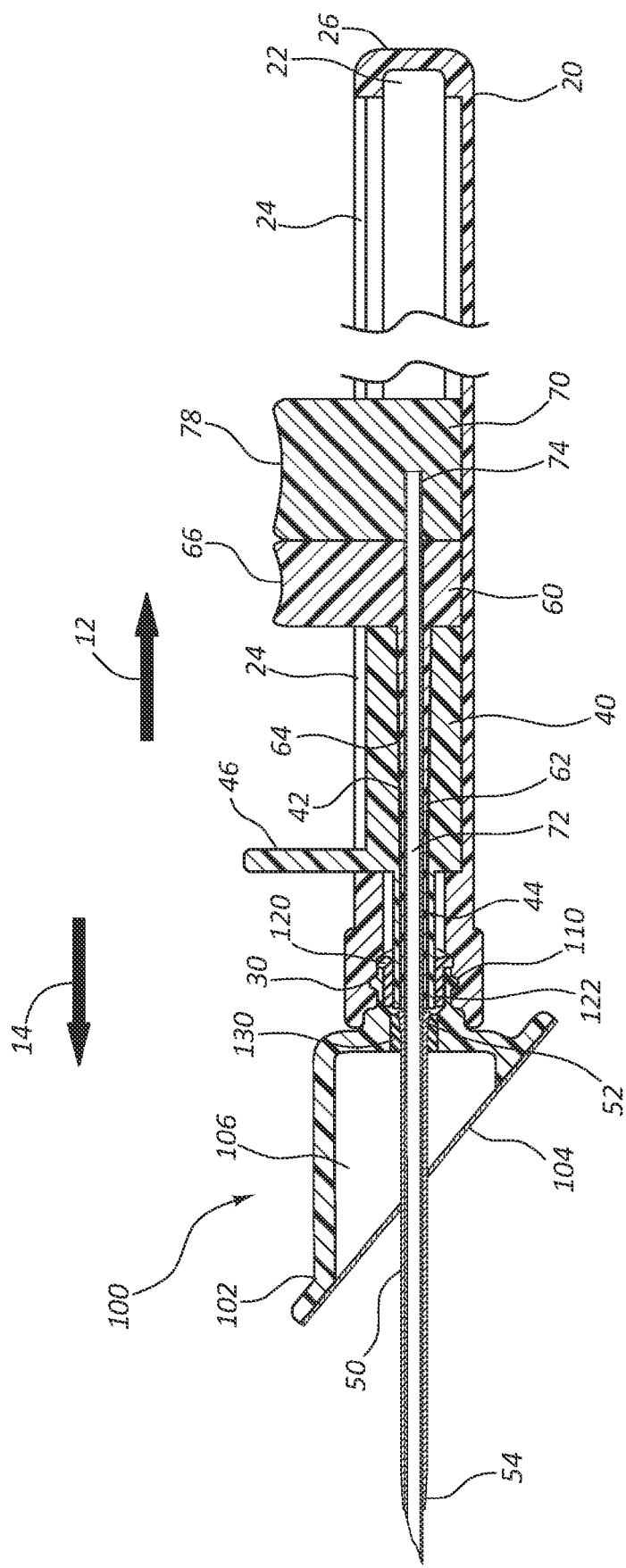
FIG. 3 illustrates a cross-section side view of an intravenous catheter inserter having the needle and catheter fully extended such that a base portion of the catheter is fully seated into a wedge seal of the Luer adapter in accordance with a representative embodiment of the present invention.

Catheter inserter device 10 may be used to insert catheter 50 into the vascular system of a patient. A non-limiting example of a method of catheterization is demonstrated in FIGS. 2-7. Referring now to FIG. 2, a first step in the catheterization process is to attach base surface 104 to a patient (not shown). In some embodiments, base portion 104 comprises a non-adhesive backing or covering (not shown) that is removed from base portion 104 to expose an adhesive for attaching hood 102 to the patient. Once Luer adapter 100 is coupled to the patient, septum activator 40 is slid in distal direction 14 such that distal end 44 is inserted through septum 120 to provide a pathway there through. In some instances, a lubricious material or coating is applied to slit 122 and/or the outer surface of distal end 44 to facilitate easy insertion of distal end 44 through slit 122. In other instances, a lubricious material or coating is applied to opening 44 and/or the interior surface of lumen 22 to facilitate easy movement of septum activator 40, catheter threader 60, and needle hub 70 during the catheterization process.

Catheter 50 and sharpened tip 76 are advanced through septum 120 via opening 42 of septum activator 40 as needle hub 70 and catheter threader 60 are advanced through lumen 22 in distal direction 14. Sharpened tip 76 pierces base portion 104 and the skin and vein of the patient to provide openings though which catheter tip 54 is inserted and advanced. Catheter threader 60 is advanced in distal direction 14 as needle hub 70 is advanced in distal direction 14. Probe 62 of catheter threader 60 passes through opening 42 thereby advancing base portion 52 of catheter 50 through septum activator 40 and into wedge seal 130. A maximum depth of insertion for catheter tip 54 is achieved as needle threader 60 contacts the proximal end of septum activator 40 and base portion 52 of catheter 50 is fully seated into wedge seal 130.

Figure 4:
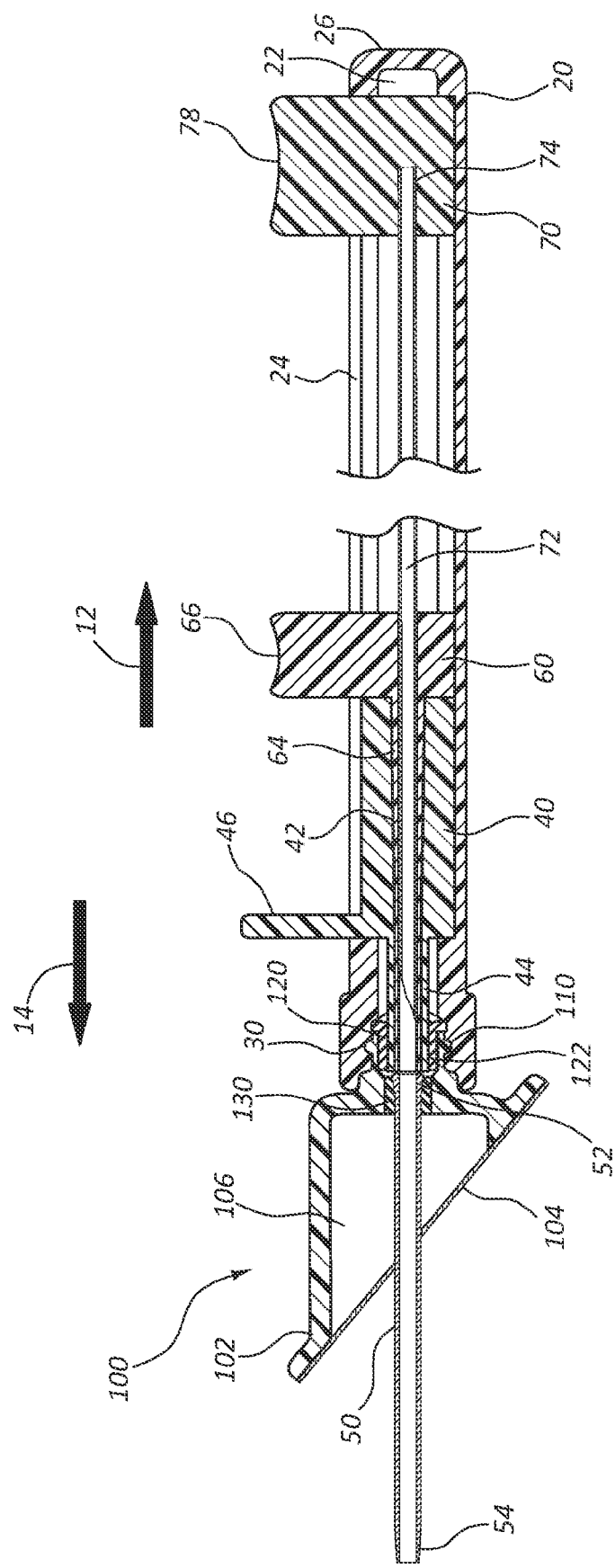
FIG. 4 is a cross-section side view of an intravenous catheter inserter following the withdrawal of the needle from the fully seated catheter in accordance with a representative embodiment of the present invention.

In some embodiments, a user may withdraw sharpened tip 76 into catheter 50 following initial insertion of catheter tip 54 into the vasculature of the patient. For example, a user may withdraw needle hub 70 in proximal direction 12. Alternatively, a user may halt movement of needle hub 70 in distal direction 14 while continuing movement of catheter threader 60 in distal direction 14, as shown in FIG. 4. The user may then proceed with advancing catheter 50 into the patient's vein by advancing catheter threader 60 in distal direction 14 independent of needle hub 70.

With continued reference to FIG. 4, following catheterization needle hub 70 is withdrawn in proximal direction 12 thereby shielding sharpened tip 76 in opening 42 of septum activator 40. Blood or other fluids from the patient are now free to flow through catheter 50 and into opening 64 of catheter threader 60. Accordingly, in some embodiments the outer diameter of needle 72 and the inner diameter of opening 64 are configured to provide minimum tolerance between the two components thereby minimizing or preventing passage of blood through opening 64. Similarly, the outer diameter of probe 62 and the inner diameter of opening 42 of septum activator 40 are configured to provide minimum tolerance between the two components thereby minimizing or preventing passage of blood through opening 42.

Figure 5:
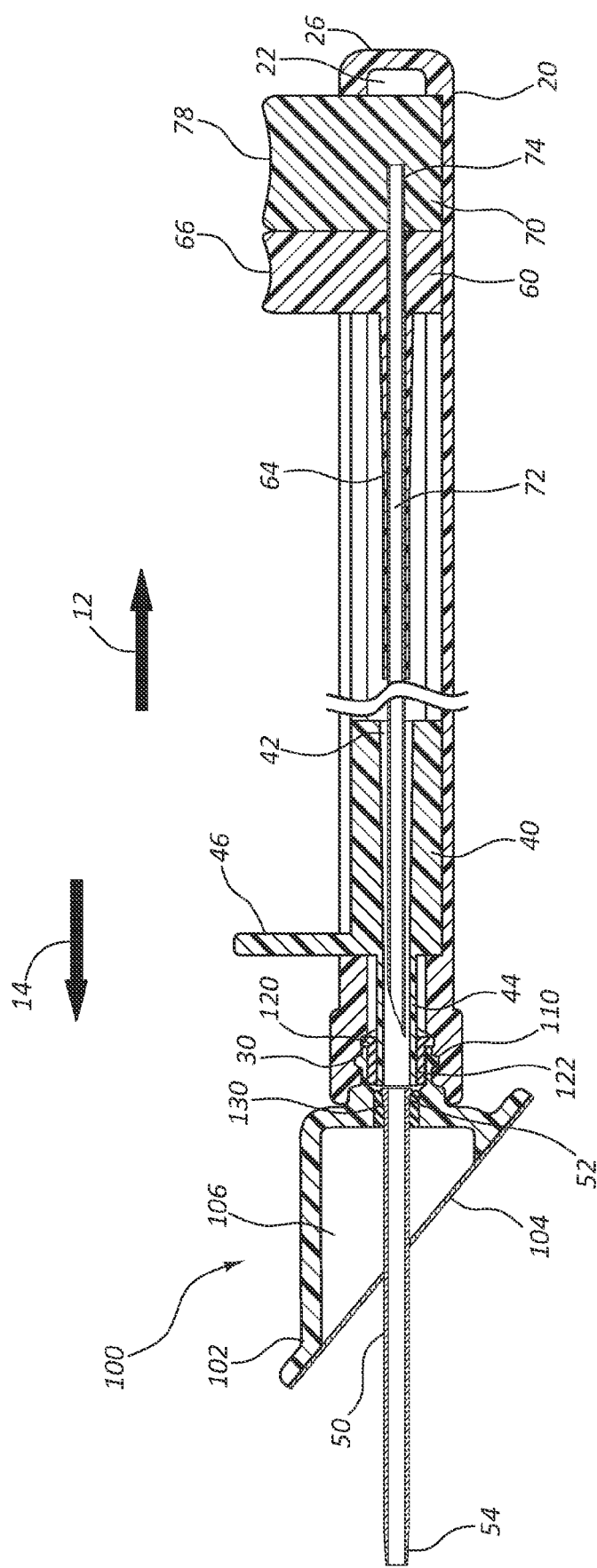
FIG. 5 is a cross-section side view of an intravenous catheter inserter following the withdrawal of the probe portion of the catheter threader from the septum actuator in accordance with a representative embodiment of the present invention.
Figure 6:
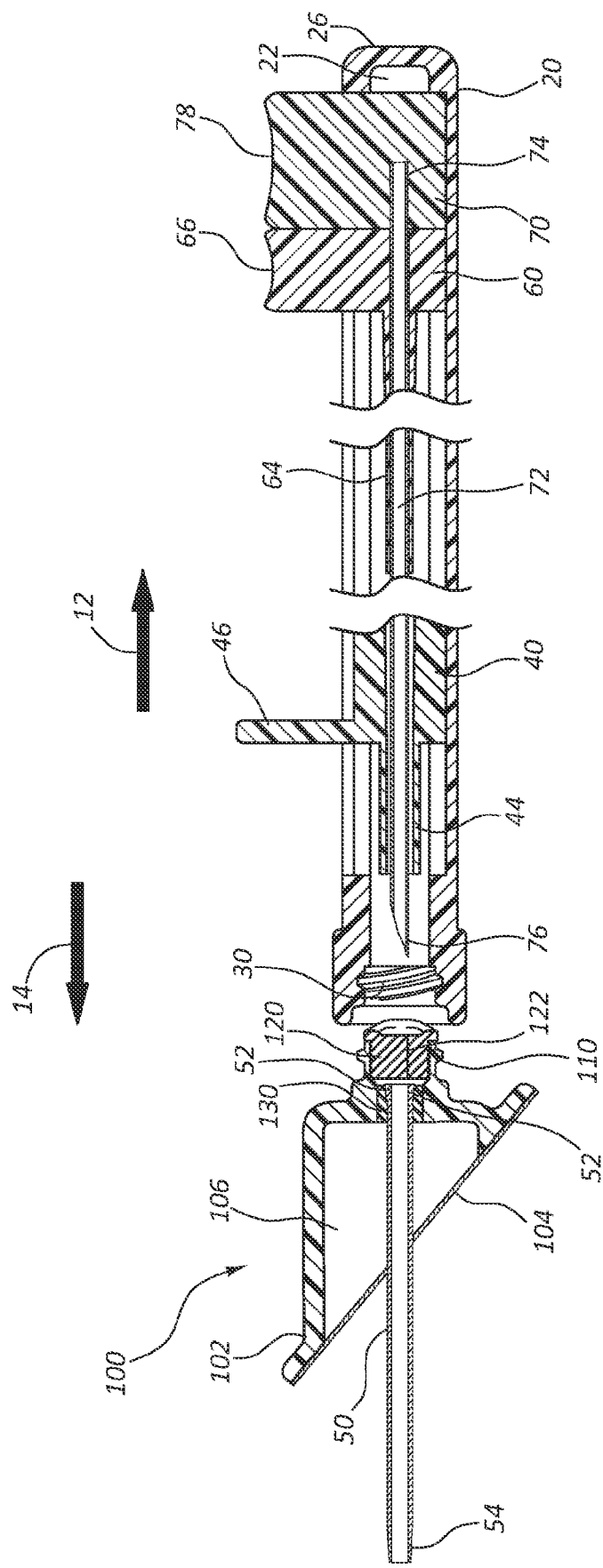
FIG. 6 is a cross-section side view of an intravenous catheter inserter detached from a Luer adapter following a catheterization procedure in accordance with a representative embodiment of the present invention.

Referring now to FIG. 5, in some embodiments, catheter threader is removed from Luer adapter 100 by moving catheter threader in proximal direction 12. As shown, removal of probe 62 from opening 42 may allow fluid communication between catheter 50 and lumen 22 via opening 42. Accordingly, in some embodiments catheter threader 60 and septum activator 40 are simultaneously moved in proximal direction 12 to prevent leakage of blood from catheter 50. The simultaneous movement of these components allows slit 122 of septum 120 to close and self-seal with minimum exposure to blood or other fluids.

Following removal of septum activator 40 from septum 120, slit 122 of septum 120 is self-sealed thereby isolating internal space 106 from an external environment. Catheter threader body 20 may then be removed from Luer adapter 100 by unthreading threads 110 and 30. Catheter threader body 20 and the various components comprised therein are then disposed.

Figure 7:
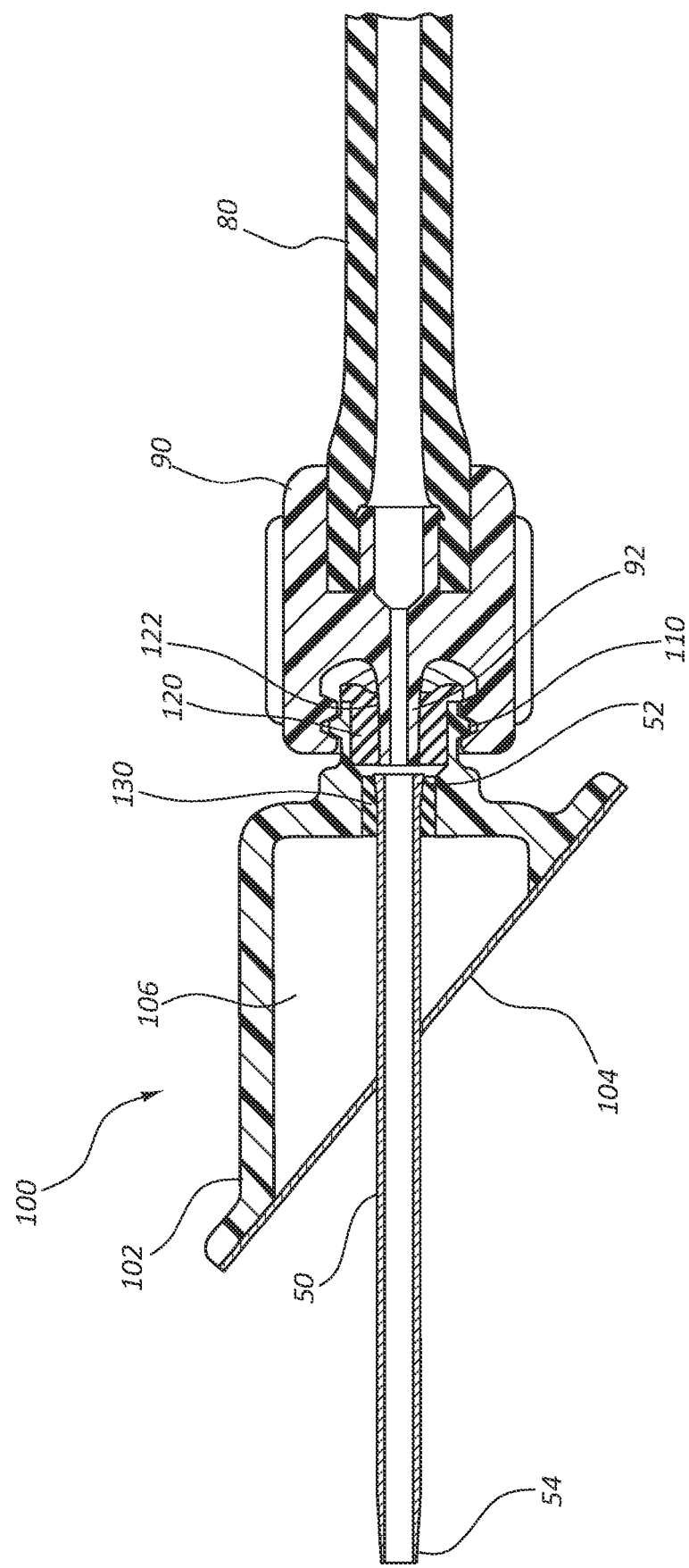
FIG. 7 illustrates a fluid line coupled to a Luer adapter following a catheterization procedure in accordance with a representative embodiment of the present invention.

The vascular system of the patient is accessed by coupling a fluid line 80 to Luer adapter 100 via a Luer connector 90, as shown in FIG. 7. In some embodiments, Luer connector 90 comprises a probe 92 that is inserted through slit 122 of septum 120 as Luer connector 90 is threadedly coupled to threads 110 of Luer adapter 100. Alternatively, the vascular system of the patient may be accessed by inserting a syringe or other device into slit 122 of septum 120.

Figure 8:
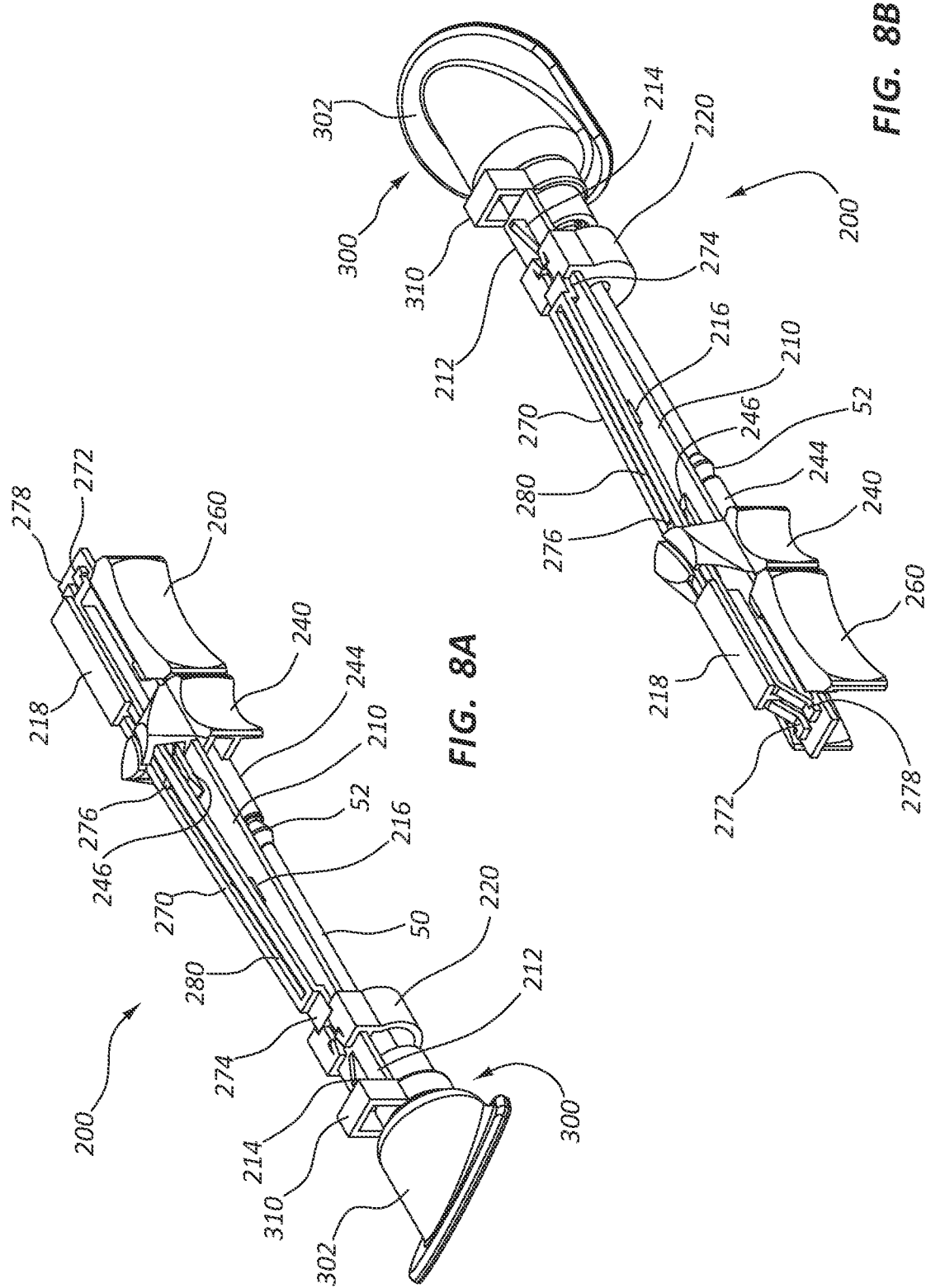
FIG. 8, shown in parts A and B, illustrates a perspective view of an intravenous catheter inserter in accordance with a representative embodiment of the present invention.
Figure 9:
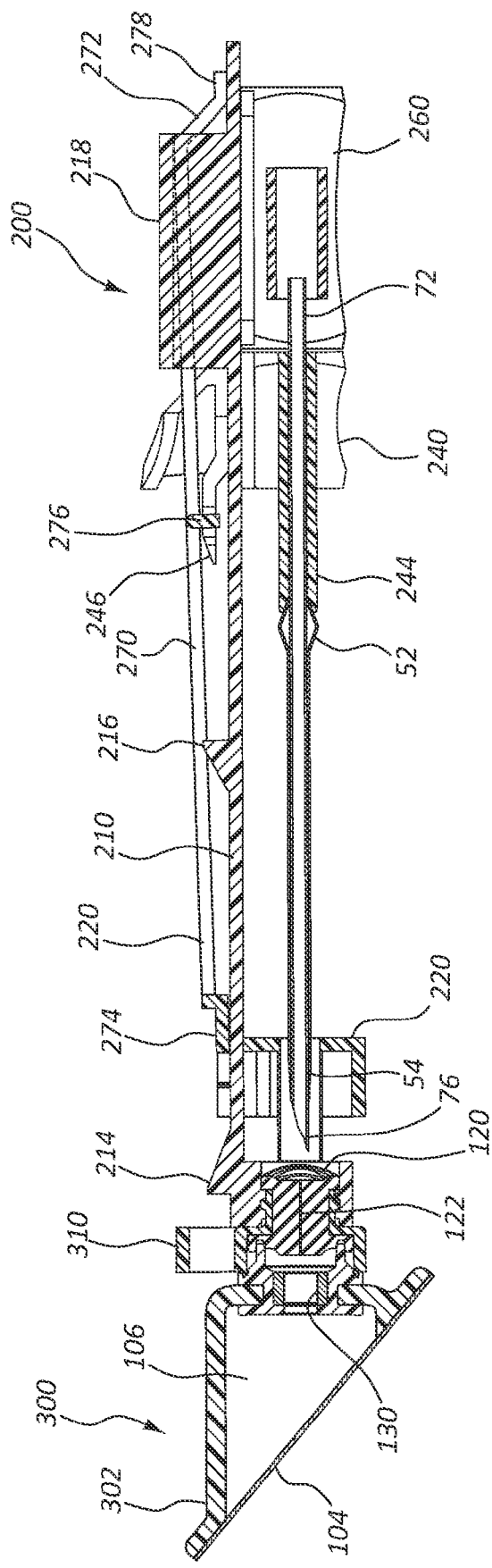
FIG. 9 illustrates a cross-section side view of the intravenous catheter inserter shown in FIG. 8 at a starting position in accordance with a representative embodiment of the present invention.

Referring now to FIGS. 8A-13C, a representative embodiment of a catheter inserter device 200 is shown. Catheter inserter device 200 comprises various safety features that prevent premature detachment of Luer adapter 300 from catheter inserter body 210. With reference to FIGS. 8A-9, catheter inserter device 200 includes a catheter inserter body 210 comprising a rail on which is slidably mounted a septum activator 220, a catheter threader 240, and a needle hub 260. Further, Luer adapter 300 comprises a rotational block or guard 310 that is positioned at a location between hood 302 and inserter body 210 during the catheterization procedure.

A probe portion 244 of catheter threader 240 is positioned beneath or under catheter inserter body 210 and is configured to compatibly receive and retain base portion 52 of catheter 50, for example by an interference fit. In some instances, base portion 52 comprises a shape that is received by a compatible shape or surface of probe portion 244. A light adhesive may also be employed between base portion 52 and probe portion 244 as may be required to facilitate forward and reverse motion of catheter 50 during catheterization. Prior to catheterization, catheter tip 54 and sharpened tip 76 of the needle 72 are shielded within septum activator 220 at a position proximate to septum 120.

Catheter inserter device 200 further comprises a safety bar 270 having a first end 272 that is slidably coupled to an upper portion of needle hub 260, and comprises a second end 274 extending distally from needle hub 260 and being positioned adjacent to septum activator 220. Prior to catheterization, second end 274 abuts and contacts a proximal end surface of septum activator 220. As such, safety bar 270 is prevented from moving in a distal direction towards Luer adapter 300. Further, a clip 246 of catheter threader 240 is secured to a tab 276 of safety bar 270 thereby locking together catheter threader 240 and safety bar 270. Accordingly, the interference between second end 274 and septum activator 220 also prevents movement of catheter threader 240 in a distal direction towards Luer adapter 300. Further still, the abutted position of needle hub 260 and catheter threader 240 prevent movement of needle hub 260.

Catheter inserter body 210 comprises various features to control movement of septum activator 220, safety bar 270, catheter threader 240, and needle hub 260 during the catheterization procedure. For example, inserter body 210 comprises a ramp 214 that is positioned on the distal end 212 of inserter body 210. Inserter body 210 further comprises a splitter 216 that is positioned approximately in the center of the length of inserter body 210. In some embodiments, splitter 216 is configured to extend upwardly within a window 280 of safety bar 270. Inserter body 210 further comprises a roof or cover 218 forming a proximal end of catheter inserter device 200. Cover 218 is provided to generally retain or control the position of first end 272 of safety bar 270 throughout the catheterization procedure.

First end 272 of safety bar 270 further comprises one or more prongs 278 that are configured to interact with needle hub 260 at various times during the catheterization procedure. For example, in some embodiments one or more prongs 278 are initially compressed and partially housed within a channel of needle hub 260. As needle hub 260 is moved in a distal direction, the one or more prongs 278 are displaced from needle hub 260 and assume an uncompressed or expanded position. As needle hub 260 returns to its initial position, the now expanded prongs catch on needle hub 260 thereby dragging safety bar 270 in a proximal direction, as will be shown.

The first step of the catheterization process is to provide a pathway through septum 120 by advancing septum activator 220 through slit 122, as shown in FIGS. 10A-10C. In some embodiments, septum activator 220 comprises a one-way clip 222 that is configured to receive and lock onto ramp 214 as septum activator is advanced in distal direction 14. In the locked position, the proximal surface of septum activator 220 is no longer interposed between ramp 214 and second end 274 of safety bar 270. Accordingly, needle hub 260, catheter threader 240, and safety bar 270 may be advanced in distal direction 14. As these components are moved in distal direction 14, second end 274 of safety bar 270 contacts the inclined surface of ramp 214 thereby lifting second end 274 over septum activator 220. Upon further advancement in distal direction 14, second end 274 of safety bar 270 is positioned within rotational block 310. Rotational block 310 comprises a compartment that is fixedly attached to Luer adapter 300. When second end 274 is positioned within rotational block 310, catheter inserter body 210 is prevented from being rotated, thereby preventing premature separation of catheter inserter body 210 from Luer adapter 300 during the catheterization process.

In the process of moving needle hub 260, catheter threader 240, and safety bar 270 in distal direction 14, clip 246 of catheter threader 240 is moved past splitter 216. Splitter 216 separates the two halves of clip 246 thereby releasing tab 276 of safety bar 270. Tab 276 contacts splitter 216 and prevents additional advancement of safety bar 270 in distal direction 14. However, catheter threader 240 is no longer coupled to safety bar 270 and may therefore continue advancing in distal direction 14 with needle hub 260, as shown in FIGS. 11A-11C. As needle hub 260 moves in distal direction 14, one or more prongs 278 are released from needle hub 260 and assume an uncompressed or expanded formation.

With continued reference to FIGS. 11A-11C, continued advancement of catheter threader 240 and needle hub 260 in distal direction 14 results in catheterization of the patient. In particular, probe 244 of catheter threader 240 advances and seats base portion 52 of catheter 50 into wedge seal 130. Septum activator 220 provides a pathway through septum 120 thereby preventing septum damage and eliminating frictional feedback between catheter 50 and septum 120 during catheterization.

Following catheterization of the patient, needle 72 is withdrawn from catheter 50 as needle hub 260 is moved in proximal direction 12. As needle hub 260 passes first end 272 of safety bar 270, uncompressed prongs 278 catch on needle hub 260 thereby dragging safety bar 270 in proximal direction 12 with needle hub 260, as shown in FIGS. 12A-12C. In a maximum proximal position of needle hub 260, second end 274 of safety bar is removed from rotational block 310 and sharpened tip 76 of needle 72 is shielded within septum activator 220. Accordingly, catheter inserter body 210 may be rotated and disconnected from Luer adapter 300, as shown in FIGS. 13A-13C. Once removed from Luer adapter 300, catheter inserter body 210 may be discarded.

In some embodiments, catheter inserter body 210 further comprises one or more safety locks 230 (see FIG. 11B) which are provided to lock needle hub 260 in a maximum proximal position following catheterization. Inserter body 210 may further include addition locks 232 to prevent removal of needle hub 260 from inserter body 210. These features prevent accidental contact with sharpened tip 76 of needle 72 before and after catheterization.

The present invention may be embodied in other specific forms without departing from its structures, methods, or other essential characteristics as broadly described herein and claimed hereinafter. All of the described embodiments and examples are to be considered in any and all respects as illustrative only, and not restrictive. The scope of the invention is, therefore, indicated by the appended claims, rather than by the foregoing description. All changes that come within the meaning and range of equivalency of the claims are to be embraced within their scope.

The invention claimed is:

1. An intravenous catheter inserter device, comprising:
   a Luer adapter having a first end comprising a septum and a second end comprising a catheter hood having a base, the Luer adapter further comprising a wedge seal interposed between the first and second ends;
   an inserter body having a distal end for receiving the first end of the Luer adapter;
   a septum activator slidably coupled to the inserter body, a distal portion of the septum activator being configured to provide a pathway through the septum, the septum activator further having an aperture;
   a catheter threader slidably coupled to the inserter body, the catheter threader having a probe for contacting a base portion of a catheter, the probe being configured to advance the base portion of the catheter through the aperture of the septum activator and the pathway through the septum and into the wedge seal, the wedge seal being configured to retain the catheter and form a fluid-tight seal between the base portion and the wedge seal, the probe further having an opening providing a pathway through the probe; and
   a needle hub slidably coupled to the inserter body and including a needle which extends through the opening of the probe, the aperture of the septum activator, the pathway through the septum, and the catheter to assist in inserting the catheter into a patient.

2. The device of claim 1, wherein the inserter body further comprises a rail on which the septum activator, the catheter threader, and the needle hub are slidably coupled.

3. The device of claim 1, wherein the inserter body further comprises a lumen in which the septum activator, the catheter threader, and the needle hub are slidably positioned.

4. The device of claim 3, further comprising a window through which a portion of the septum activator, the catheter threader, and the needle hub extends to provide access to a user.

5. The device of claim 2, further comprising a safety bar having a first end and a second end, the first end being slidably coupled to the needle hub, and the second end extending distally from the needle hub and being positioned adjacent to a distal end of the rail.

6. The device of claim 5, wherein the catheter threader further comprises a clip that is configured to retain a tab of the safety bar.

7. The device of claim 6, wherein the rail further comprises a splitter which is configured to contact the clip of the catheter threader and release the tab of the safety bar as the catheter threader and the safety bar are moved in a distal direction, and wherein contact between the splitter and the tab of the safety bar limits movement of the safety bar in the distal direction.

8. The device of claim 5, wherein the distal end of the rail further comprises a ramp and the Luer adapter further comprises a rotational block.

9. The device of claim 8, wherein the septum activator comprises a clip that is configured to receive the ramp and lock the septum activator to the ramp in a locked position, wherein the locked position results in the distal portion of the septum activator being inserted through the septum to provide the pathway through the septum.

10. The device of claim 9, wherein the ramp further comprises an inclined surface which is contacted by the second end of the safety bar as the needle hub and the safety bar are moved in a distal direction, wherein contact between the inclined surface and the safety bar lifts the second end of the safety bar over the septum activator to insert the second end of the safety bar into the rotational block.

11. The device of claim 5, wherein the first end of the safety bar further comprises one or more prongs that are compressed within and slidably connected to a channel of the needle hub, wherein the one or more prongs exit the channel of the needle hub as the needle hub is moved in a distal direction, the one or more prongs thereby becoming uncompressed such that a width of the one or more prongs is greater than a width of the channel whereby the one or more prongs catches on a proximal end of the needle hub as the needle hub is moved in a proximal direction.

12. The device of claim 1, wherein the wedge seal comprises an annular seal having an inner diameter that is configured to receive the base of the catheter.

13. A method for manufacturing an intravenous catheter inserter, the method comprising:
  providing a Luer adapter having a first end comprising a septum and a second end comprising a catheter hood having a base;
  positioning a wedge seal within the Luer adapter at a positioned between the first and second ends;
  providing an inserter body having a distal end for receiving the first end of the Luer adapter;
  slidably coupling a septum activator to the inserter body, a distal portion of the septum activator being configured to provide a pathway through the septum, the septum activator further having an opening;
  slidably coupling a catheter threader to the inserter body, the catheter threader having a probe for contacting a base portion of a catheter, the probe being configured to advance the base portion of the catheter through the opening of the septum activator and the pathway through the septum and into the wedge seal, the wedge seal being configured to retain the catheter and form a fluid-tight seal between the base portion and the wedge seal, the probe further having an opening for providing a pathway through the probe; and
  slidably coupling a needle hub to the inserter body, the needle hub having a needle which extends through the opening of the probe, the opening of the septum activator, and the catheter, wherein the needle assists in inserting the catheter into a patient.

14. The method of claim 13, wherein the inserter body further comprises a rail on which the septum activator, the catheter threader, and the needle hub are slidably coupled.

15. The method of claim 13, wherein the inserter body further comprises a lumen in which the septum activator, the catheter threader, and the needle hub are slidably positioned.

16. The method of claim 15, further comprising a step for providing a window in the inserter body to provide access to the septum activator, the catheter threader, and the needle hub.

17. The method of claim 13, further comprising a step for providing a safety bar having a first end and a second end, the first end being slidably coupled to the needle hub, the second end extending distally from the needle hub and being positioned adjacent to a distal end of the rail.

18. The method of claim 17, further comprising a step for providing a clip on the catheter threader, the clip being configured to retain a tab of the safety bar.

19. The method of claim 18, further comprising a step for providing a splitter on the rail which is configured to contact the clip of the catheter threader and release the tab of the safety bar as the catheter threader and the safety bar are moved in a distal direction, and wherein contact between the splitter and the tab of the safety bar limits movement of the safety bar in the distal direction.

20. The method of claim 19, further comprising:
  providing a ramp on the distal end of the rail;
  providing a rotational block on the Luer adapter; and
  providing a clip on the septum activator, the clip being configured to receive the ramp and lock the septum activator to the ramp in a locked position, the locked position resulting in the distal portion of the septum activator being inserted through the septum to provide the pathway through the septum, the ramp further comprising an inclined surface which is contacted by the second end of the safety bar as the needle hub and the safety bar are moved in a distal direction, wherein contact between the inclined surface and the safety bar lifts the second end of the safety bar over the septum activator to insert the second end of the safety bar into the rotational block.

* * * * *